(12) United States Patent
Brueck et al.

(10) Patent No.: US 10,411,436 B2
(45) Date of Patent: Sep. 10, 2019

(54) ROBUST, COMPACT, FIELD-ABLE TUNABLE INTEGRATED PHOTONIC DEVICE

(71) Applicant: STC.UNM, Albuquerque, NM (US)

(72) Inventors: Steven R. J. Brueck, Albuquerque, NM (US); Sanjay Krishna, Albuquerque, NM (US); Daniel P. Dapkus, Fullerton, CA (US)

(*) Notice: Subject to any disclaimer, the term of this patent is extended or adjusted under 35 U.S.C. 154(b) by 0 days.

(21) Appl. No.: 15/571,800

(22) PCT Filed: May 6, 2016

(86) PCT No.: PCT/US2016/031301
§ 371 (c)(1),
(2) Date: Nov. 3, 2017

(87) PCT Pub. No.: WO2017/023387
PCT Pub. Date: Feb. 9, 2017

(65) Prior Publication Data
US 2018/0366904 A1 Dec. 20, 2018

Related U.S. Application Data

(60) Provisional application No. 62/158,129, filed on May 7, 2015.

(51) Int. Cl.
*H01S 5/00* (2006.01)
*H01S 5/12* (2006.01)
(Continued)

(52) U.S. Cl.
CPC .......... *H01S 5/1218* (2013.01); *H01S 5/0085* (2013.01); *H01S 5/021* (2013.01); *H01S 5/0268* (2013.01); *H01S 5/02248* (2013.01); *H01S 5/041* (2013.01); *H01S 5/042* (2013.01); *H01S 5/0421* (2013.01); *H01S 5/1212* (2013.01);
(Continued)

(58) Field of Classification Search
CPC ...... H01S 5/1212; H01S 5/041; H01S 5/4087; H01S 5/0085; H01S 5/02248; H01S 5/021; H01S 5/042; H01S 5/02208; H01S 5/0425; H01S 5/34306; H01S 5/0421;
(Continued)

(56) References Cited

U.S. PATENT DOCUMENTS 4,815,084 A * 3/1989 Scifres ................. H01S 5/0425
257/98
5,515,391 A 5/1996 Endritz
(Continued)

OTHER PUBLICATIONS

Kishkovich, O., (Authorized PCT Officer), "PCT Notification of Transmittal of the International Search Report and the Written Opinion of the International Searching Authority, or the Declaration," dated Feb. 27, 2017.

*Primary Examiner* — Kinam Park
(74) *Attorney, Agent, or Firm* — MH2 Technology Law Group, LLP

(57) ABSTRACT

A tunable laser device includes a laser structure and a plurality of individually addressable, separated contact stripes disposed on the laser structure. The laser structure includes a substrate, an active portion disposed on the substrate, and a chirped distributed feedback (DFB) grating disposed on the active portion. The active portion includes at least top and bottom contact layers and a gain medium.

39 Claims, 10 Drawing Sheets

(51) Int. Cl.
*H01S 5/042* (2006.01)
*H01S 5/026* (2006.01)
*H01S 5/02* (2006.01)
*H01S 5/022* (2006.01)
*H01S 5/04* (2006.01)
*H01S 5/40* (2006.01)
H01S 3/13 (2006.01)
H01S 5/50 (2006.01)
H01S 5/343 (2006.01)
G01N 21/17 (2006.01)
G01N 21/39 (2006.01)

(52) U.S. Cl.
CPC .... *H01S 5/4087* (2013.01); *G01N 2021/1704* (2013.01); *G01N 2021/394* (2013.01); *G01N 2021/399* (2013.01); *H01S 3/1303* (2013.01); *H01S 5/02208* (2013.01); *H01S 5/0425* (2013.01); *H01S 5/34306* (2013.01); *H01S 5/50* (2013.01)

(58) Field of Classification Search
CPC ........ H01S 5/0268; H01S 5/1218; H01S 5/50; H01S 3/1303; G01N 2021/394
See application file for complete search history.

(56) References Cited

U.S. PATENT DOCUMENTS

| | | |
|---|---|---|
| 6,104,739 A | 8/2000 | Hong et al. |
| 7,092,589 B2 | 8/2006 | Kish, Jr. et al. |
| 2003/0091081 A1 | 5/2003 | Sahara et al. |
| 2008/0240174 A1 | 10/2008 | Brueck et al. |

* cited by examiner

ROBUST, COMPACT, FIELD-ABLE TUNABLE INTEGRATED PHOTONIC DEVICE

CROSS-REFERENCE TO RELATED APPLICATIONS

This application is a U.S. National Phase application of PCT/US2016/031301 filed 6 May 2016, which claims priority to U.S. Provisional Application Ser. No. 62/151,129, filed May 7, 2015, the entirety of which is incorporated herein by reference.

GOVERNMENT RIGHTS

This disclosure was made with Government support under Contract No. FA9550-12-1-0480 awarded by the Air Force Office of Scientific Research. The Government has certain rights in the invention.

TECHNICAL FIELD

Embodiments described herein relate generally to photonics, particularly to generation, emission, control, and detection or sensing of light via integrated photonic source.

BACKGROUND

The mid-infrared 3 to 5 µm atmospheric transmission window is important for remote sensing and spectroscopic applications because it contains many fingerprint molecular rotation-vibrational absorption lines, such as O—H stretch at 2.8 µm; N—H stretch at ~3 µm, C—H stretch at ~3.3 µm. Spectroscopic applications typically require a continuous wave (CW), single-longitudinal-mode (SLM) and mode-hop-free, continuously tunable, narrow spectral linewidth, high power laser source with good beam quality.

Imaging systems for identifying gas leaks are one such spectroscopic application. These systems function by emitting a laser beam through a gas and capturing an image of light with an MIR imager. The light from the laser beam is backscattered by the gas or objects positioned near the gas, or backscattered light that is absorbed by the gas. Such conventional imaging systems incorporate complex photonic integrated circuits.

There has been much interest in the design, manufacture, testing, assembly, and packaging of complex photonic integrated circuits that combine a variety of photonic and electronic components to achieve functionality. The demonstration of integrated photonic sensors that are manufacturable and scalable to reduce size, weight, power, and cost is pivotal for success in this industry. Current breadboard technologies used as integrated photonic sources contain critical alignment issues and fail to reduce size, weight, power, and cost of product.

Thus, what is needed is a more compact and tunable integrated photonic source that overcomes the limitations of current technologies.

SUMMARY

In an embodiment there is a tunable laser device that comprises a laser structure and a plurality of individually addressable, separated contact stripes disposed on the laser structure. The laser structure comprises a substrate, an active portion disposed on the substrate, and a chirped distributed feedback (DFB) grating disposed on the active portion. The active portion comprises at least top and bottom contact layers and a gain medium.

In another embodiment, there is a method of operating a tunable laser device, comprising: electrically pumping a laser structure, the laser structure comprising: a substrate, an active portion disposed on the substrate, wherein the active portion comprises at least top and bottom contact layers and a gain medium, and a chirped distributed feedback (DFB) grating disposed on the active layer, wherein the electrically pumping of the laser structure comprises applying a distribution of currents to different ones of a plurality of separated contact stripes formed on the laser structure.

In another embodiment, there is method of forming a tunable laser device, comprising: providing a laser structure comprising: a substrate, an active layer disposed on the substrate, and a chirped distributed feedback (DFB) grating disposed on the active layer; forming a contact layer on the laser structure, the contact layer comprising a doped gain medium; forming a blanket layer on the contact layer; patterning the blanket layer into a grating pattern by etching portions thereof to expose the contact layer; and forming a plurality of separated contact stripes on the laser structure substantially normal to the grating pattern.

In another embodiment, there is an integrated photonics laser source, comprising: a laser chip that provides a spatially varying electromagnetic output, the laser chip comprising an electronically pumped laser source having a plurality of individually addressable, separated contact stripes formed thereon; and an integrated optic Si/III-V chip, comprising: an array waveguide (AWG) that takes the spatially varying output of the laser chip and funnels it into a single waveguide, a modulator for modulating a frequency of electromagnetic energy from the single waveguide, a beam splitter that redirects the electromagnetic output from the modulator, a reference gas disposed in a hermetically sealed gas cell for absorbing at least some of the redirected electromagnetic output, and an acoustics detector for monitoring absorption of the reference gas; and a power amplifier.

In another embodiment, there is a method for photonically sensing chemicals, comprising: providing an integrated photonics chemical source, the source comprising: a laser chip that provides a spatially varying electromagnetic output, an integrated optic Si/III-V chip, and a power amplifier, wherein the laser chip comprises a chirped grating to provide continuous tuning of a broadband gain medium, a plurality of separated contact stripes, and a plurality of pump fingers for electrical pumping, and wherein the integrated optic Si/III-V chip comprises: a modulator for modulating a frequency of electromagnetic energy from the single waveguide, a beam splitter that redirects the electromagnetic output from the modulator, a reference gas disposed in a hermetically sealed gas cell for absorbing at least some of the redirected electromagnetic output, and an acoustics detector for monitoring absorption of the reference gas; and pumping two or more separated groups of stripes at the same time.

Advantages can include one or more of the following: increased reliability and vibration/environmental insensitivity through utilization of chirped grating as compared with external cavity configurations; integrated photonic sensors that are manufacturable and scalable to reduce size, weight, power, and cost; accurate frequency calibrations due to gas cell/photo-acoustic spectroscopy; a power amplifier that allows for increased sensing distances (km); room temperature operability; and applications in telecommunications, chemical sensing that include wide area surveillance, toxic industrial chemicals, leak detection, manufacturing process, and environmental monitoring Additional advantages of the embodiments will be set forth in part in the description which follows, and in part will be understood from the description, or may be learned by practice of the embodiments. The advantages will be realized and attained by means of the elements and combinations particularly pointed out in the appended claims.

It is to be understood that both the foregoing general description and the following detailed description are exemplary and explanatory only and are not restrictive of the embodiments, as claimed.

BRIEF DESCRIPTION OF THE DRAWINGS

The accompanying drawings, which are incorporated in and constitute a part of this specification, illustrate embodiments of the present teachings and together with the description, serve to explain the principles of the disclosure.

FIG. 5A is a cross sectional view from the side of a laser device and FIG. 5B is a top-view of the laser device of FIG. 5A.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g., −1, −2, −3, −10, −20, −30, etc.

The following embodiments are described for illustrative purposes only with reference to the figures. Those of skill in the art will appreciate that the following description is exemplary in nature, and that various modifications to the parameters set forth herein could be made without departing from the scope of the present embodiments. It is intended that the specification and examples be considered as examples only. The various embodiments are not necessarily mutually exclusive, as some embodiments can be combined with one or more other embodiments to form new embodiments. It will be understood that the structures depicted in the figures may include additional features not depicted for simplicity, while depicted structures may be removed or modified.

Figure 1:
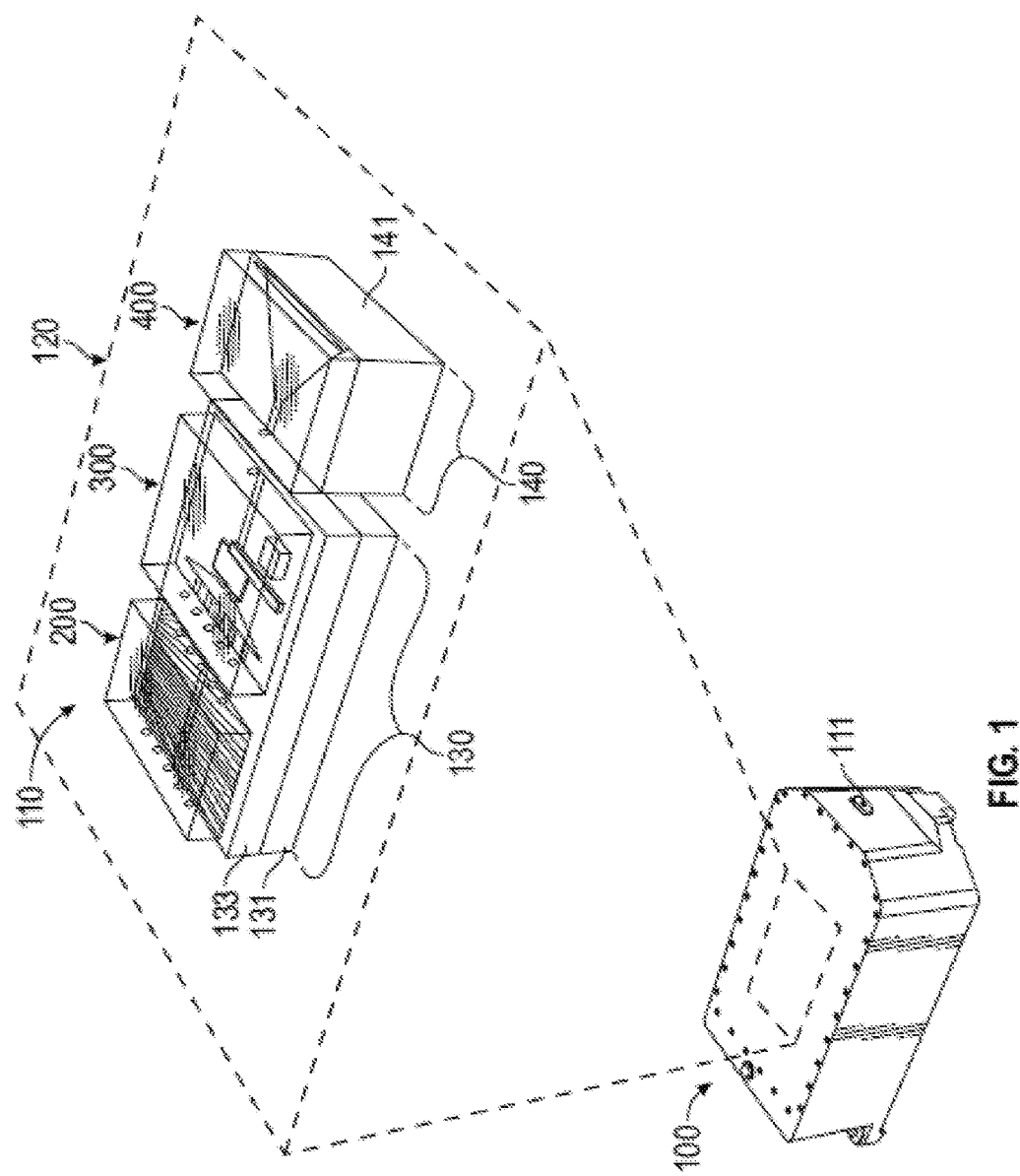
FIG. 1 illustrates an optics source that may be used for detecting and/or identifying a target gas. The inset in FIG. 1 shows internal components of the source's integrated systems, including a laser chip, an optics chip and an optional power amplifier.

Embodiments described herein provide an integrated photonics laser source that can be used in a variety of applications such as telecommunications, chemical sensing, environmental monitoring, and others. As shown in FIG. 1, an embodiment of an integrated photonics source 120 is disposed in a housing 100. The photonics source 120 comprises an integrated system 110 that includes a filter portion 130 and a power unit 140 for powering the filter portion. Filter portion 130 may include a laser chip 200, an integrated optic chip 300. Power unit 140 may include an optional power amplifier 400. Housing 100 in which photonics source 120 is disposed may include a window 111 through which a laser beam generated by integrated photonics source 120 may pass.

As explained in more detail below, the laser chip 200 may include a tunable laser having a chirped grating for tunability. Additionally, the integrated optic chip 300 may include an array waveguide (AWG) to direct the spatially variable output channels to a common on-silicon (Si) waveguide platform, an integrated modulator to avoid chirp, and a photo-acoustic spectroscopy unit (e.g., gas filled cell and acoustic wave detector) for absolute frequency calibration. The laser chip 200 and integrated optic chip 300 may share common silicon-based driver electronics at layer 133 which may be disposed on a heat sink 131. With the optional power amplifier 400, the photonics source 120 may be provided with increased sensing distances.

Due to the miniaturization of the integrated system 110, the photonics source 120 can have dimensions that make it field-ready and portable. For example, such an integrated system can be disposed in a housing having external dimensions of about 5×5×10 cm$^3$.

Laser Chip

Figure 2:
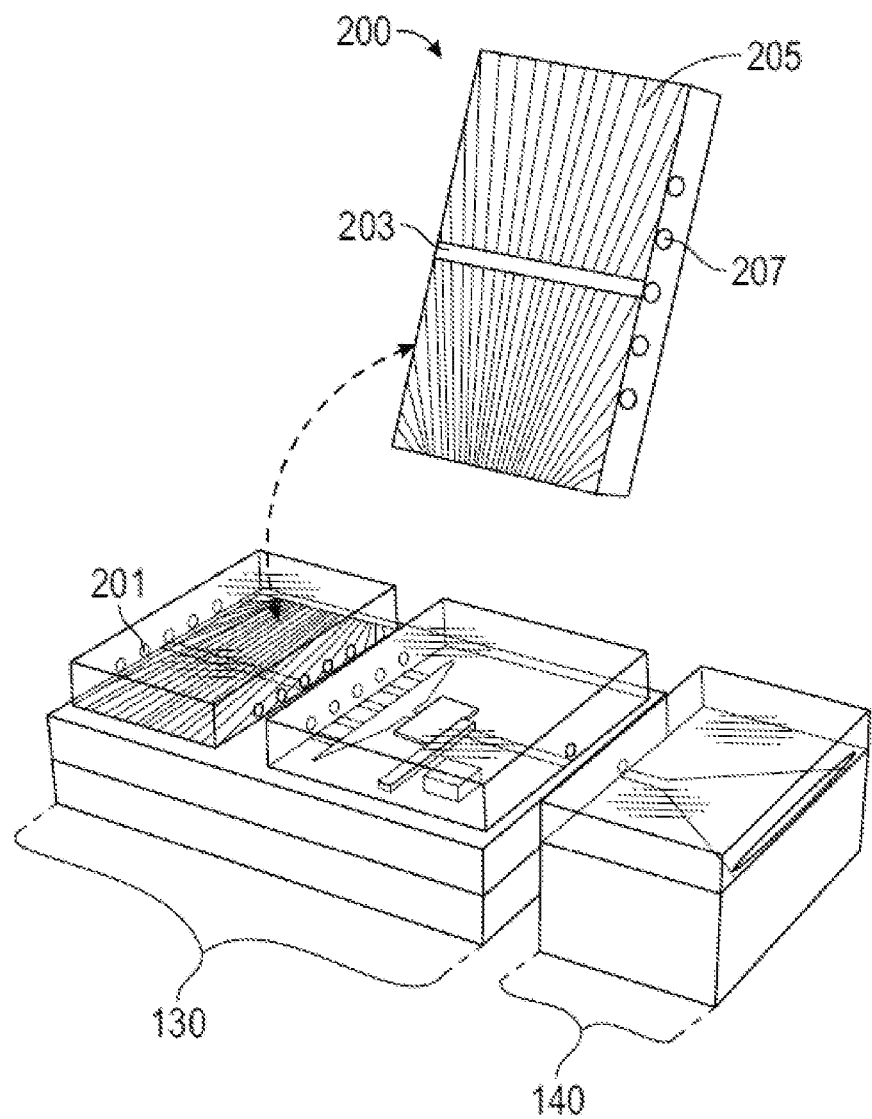
FIG. 2 shows a detailed view of the laser chip component in the integrated system of FIG. 1.

As shown in more detail in FIG. 2, the laser chip 200 is provided with continuous, mode-hop-free, wavelength tuning. In an embodiment, laser chip 200 may include a chirped grating, for example, a chirped distributed feedback (DFB) grating 205 to provide continuous tuning of a broadband gain medium. Continuous wavelength tunability without frequency gaps or mode jumps is an important characteristic for spectroscopy. In traditional unchirped DFB lasers, mode hopping can occur between the two degenerate DFB modes on either side of the stop band. This degeneracy can be lifted by introducing an asymmetry that favors one mode over the other, for example metal grating lines that have more loss for the standing wave mode with intensity maxima at the line positions. Here, a longitudinal chirp of the chirped grating 205 provides such asymmetry. Accordingly, the laser chip 200 may include a tunable laser device such as that shown in FIG. 5A, which may be a tunable mid-IR laser.

Figure 5A:
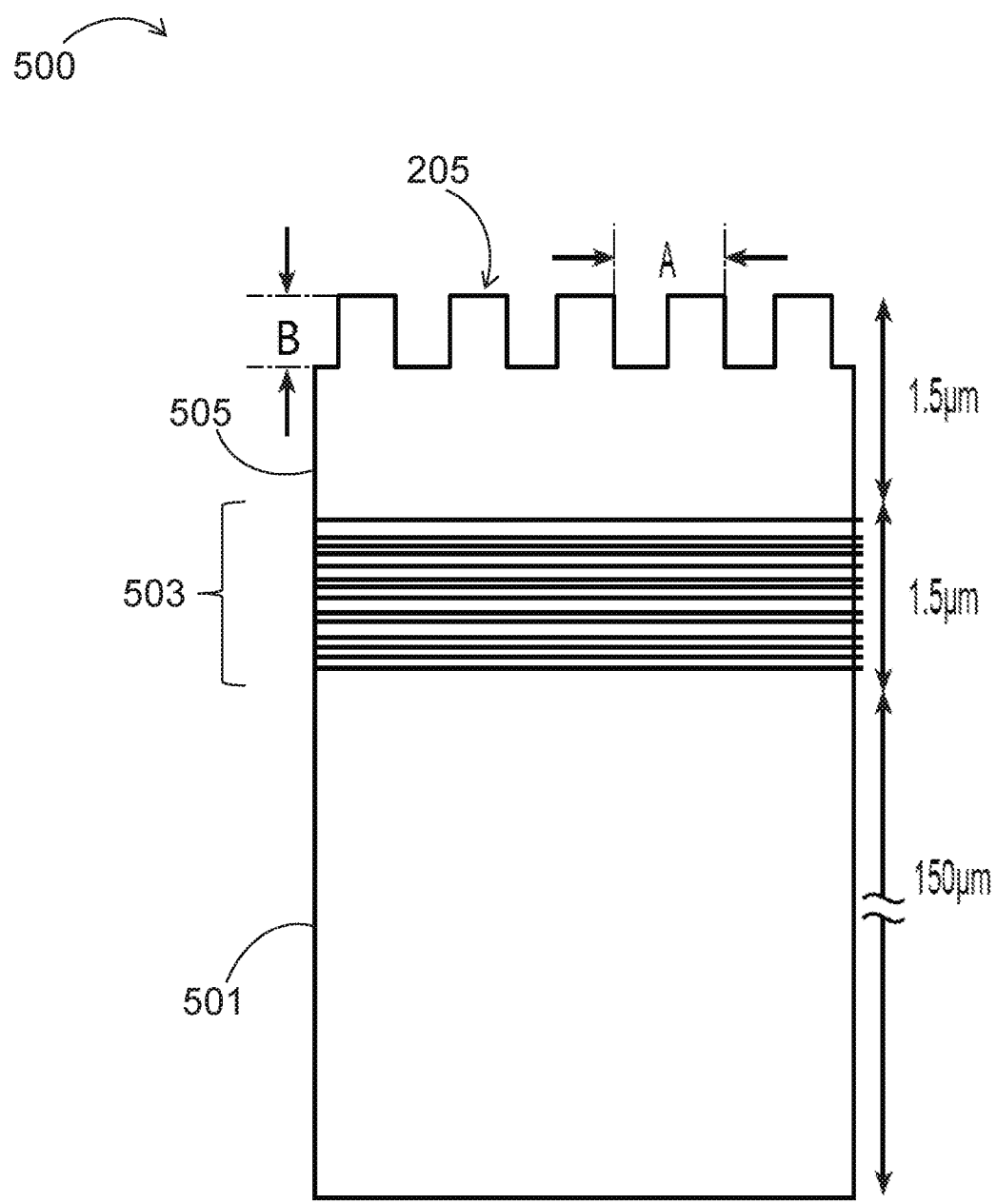
FIGS. 5A-5B show example laser device configurations.

In an example, the tunable laser device 500 may comprise a three-layer slab waveguide grown on a substrate 501 as shown in FIG. 5A, wherein the substrate 501 functions as the bottom cladding layer of the waveguide. The three-layer slab waveguide, tunable laser device 500 can also include a core 503 disposed on the substrate 501 and a top cladding layer 505 disposed on the core 503. In an embodiment, the substrate 501 may comprise GaSb, for example a Te-doped GaSb substrate. In such an embodiment of a tunable laser device, a chirped DFB grating 205 is disposed on an optically or electrically pumped laser structure (not visible in this view), wherein the chirped DFB grating comprises a grating pitch that varies across the structure and is characterized by both longitudinal and transverse chirp parameters.

In an embodiment, the core 503 can function as an active layer and may comprise a one or more quantum wells, for example type-II quantum well active regions in the GaSb/InAs or related material system such that the material optical gain is in the mid-infrared spectral region. The related material systems can include systems where the InAs is replaced by InGaAs or other ternary compound and similarly the GaSb is replaced with ternary compound such as InGaSb, for example one or more of evenly spaced type-II InAs/InGaSb/InAs quantum wells as a gain medium sandwiched between integrated absorber layers that may fully absorb pump laser power for efficient carrier confinement. In an example, the substrate 501 can have a thickness of about 150 μm, the core can have a thickness of about 1.5 μm and the top cladding layer can have a thickness of about 1.5 μm. The refractive indices of the bottom/top cladding layers can be about 3.82 and that of the core layer can be about 3.842.

The top cladding layer 505 can comprise the grated surface (i.e., a grating) having straight or hyperbolically chirped grating. In an embodiment the grated surface of the top cladding layer comprises the chirped DFB grating 205. The chirped DFB grating 205 can have a grating period adjusted to provide the feedback and to provide an output coupling normal to the plane of the chirped DFB grating. In an example, the DFB grating can have a continuously-varying grating period. In implementations, the chirped DFB grating provides a feedback essentially perpendicular to grating lines of the chirped DFB grating while the transverse chirp is principally arranged in a direction parallel to the grating lines of the chirped grating DFB grating. In another example, the laser chip may include a discrete set of DFB gratings wherein each DFB grating "B" comprises a fixed grating period "A" and the chirp is realized in different fixed grating periods. In an example, the laser chip has chirped grating with a grating period range of from 410 to 420 nm and is therefore provided with continuous, mode-hop-free, wavelength tuning range of about 80 nm to 100 nm, for example about 80 nm from 3047 nm to about 3137 nm, at 2.5×threshold pump power.

Figure 5B:
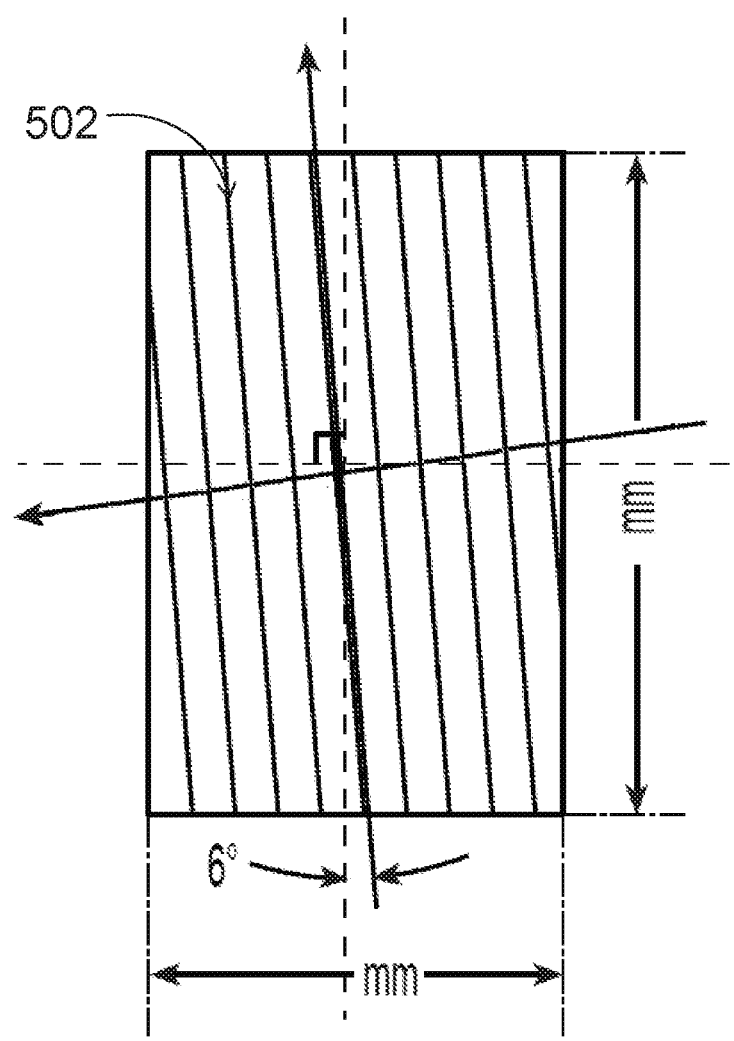

In implementations, grating lines of the chirped DFB grating can be arranged at a tilt to one or more edges of the tunable, pumped laser structure to reduce an impact of any Fabry-Perot (F-P) resonances (i.e., Fabry-Perot mode) on the lasing emission. That is, the chirped DFB grating can be arranged at a degree of tilt sufficient to eliminate facet reflections As shown for chirped grating 502 FIG. 5B, and similarly, chirped grating 504 in FIG. 5C, which illustrate top views of exemplary implementations of the tunable laser device 500, the chirped DFB grating 205 can be arranged at a tilt of about 6° relative to an edge.

The chirped DFB grating 205 can be formed by known methods. For example, a hyperbolically chirped, location-dependent-period grating for wavelength tuning, can be patterned on the top cladding layer using interferometric lithography (IL) in photoresist (PR) which may then be transferred into the top clad of the slab waveguide for wavelength selection and tuning using Cl-based inductively-coupled plasma (ICP) etching. The material for the top cladding may be selected from one or more of Ge, GaSb, AlGaSb, AlAsSb, AlGaAsSb, InAlAsSb, GaAlAsSb, AlSb, AlInSb, AlSbAs, or AlGaSbAs. In an example, a hyperbolically chirped grating can be generated by interference between two spherical wave fronts, using a 355 nm 3rd harmonic Nd:YAG laser as the coherent light source.

Figure 5C:
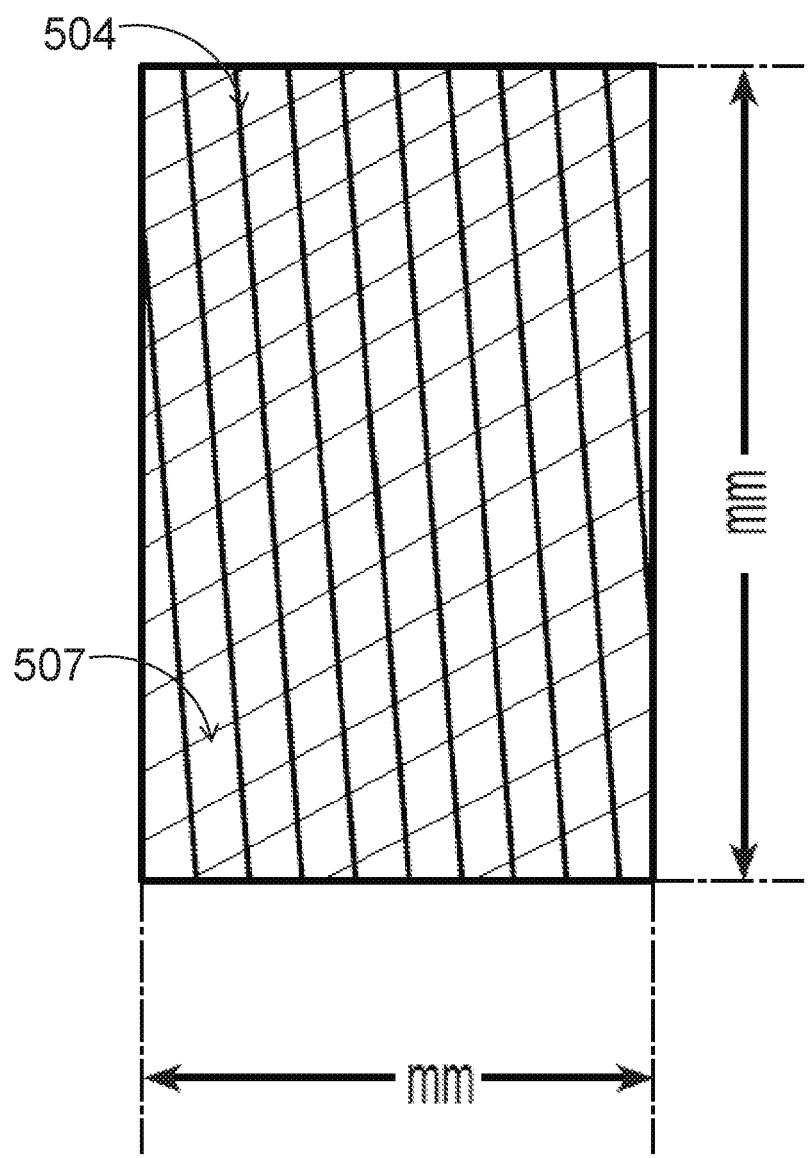
FIG. 5C shows a top view of an optically pumped laser device.

The laser structure may utilize optical or electrical pumping. FIG. 5C shows a top view of an exemplary optically pumped, tunable mid-IR laser (3-5 μm) based on type-II InAs:GaSb active regions. Such broad tuning is based on an optically addressed chirped grating fabricated by interferometric lithography (IL) over the large area device (2.5×4 mm$^2$) a pump laser provides a pump beam illumination in a sub-area with respect to an area covered by the chirped DFB grating, the position being changed to allow a continuous tuning of a lasing emission wavelength from the optically pumped laser structure. Additionally for the optically pumped laser structure, translation of the laser chip is required and could eliminate the need for the AWG discussed below.

In an example of an optically pumped laser device, wavelength tuning of the DFB laser device 500 is achieved by optically pumping a stripe across different regions of the chirped grating 502 translating an optical pump stripe across the chirp, for example, normal to the grating. In other words, pump beam illumination can be arranged in a stripe geometry with the long axis of the stripe essentially perpendicular to the lines of the grating on the sample (e.g., at 6° to the facets). In an example, optical pump stripe may have width of ~100 microns. A CW 1.908 μm thulium fiber laser can be used as for optical pumping. In implementations, the pump beam is provided from a top side of the optically pumped laser structure that is through the chirped DFB grating or from a bottom side of the optically pumped laser structure that is opposite the chirped DFB grating.

Meanwhile, FIG. 5D shows a top view of an electrically pumped, tunable mid-IR laser (3-5 μm) based on type-II InAs:GaSb active regions. In operation, tuning of the electrically pumped laser device is based on an electrically addressed chirped grating 504. Accordingly, in an example, an electrically pumped laser device has the same three-layer waveguide structure as described above for laser device 500 in FIG. 5A, has a chirped grating 504 which may have same or different features as that described for chirped grating 502 in FIG. 5B, and further comprises a plurality of separated contact stripes 507. The plurality of separated contact stripes are shown in FIG. 5D as top-side contacts, but other implementations are not so limited and the separated contact stripes may be placed anywhere so as to remain in electrical communication with the upper cladding layer.

The plurality of separated contact stripes 504 may be individually addressed by a controller (not shown) in electrical communication with the contact stripes and which may be incorporated in the device electronics of layer 133 of FIG. 1. In an implementation, current supplied to the laser (i.e., a distribution of currents applied to different ones of the plurality of separated contact stripes) may be adjusted to move the gain stripe relative to the chirped grating. For example, two or three stripes may be pumped with an analog current source so that the center of the gain can be adjusted smoothly between the strip positions. Accordingly, a controller, which may be an analog current source, may be configured to provide a distribution of currents in different ones of the plurality of contact stripes. In other words, the controller may be configured to apply a first current to a first one of the plurality of contact stripes and a second current to a second one of the plurality of contact stripes.

Two or more separated groups of stripes may be optically or electrically pumped at the same time, for example, to have one wavelength on resonance and one off resonance with a given molecular absorption. This is known as differential absorption Light Detection and ranging (LIDAR or DIAL). In one embodiment, a lasing system that utilizes two lasers or a switching between two wavelengths of the same laser may be utilized, for example a type-II W-structure that may be cooled to 77 K. In another embodiment, a room temperature lasing system may be utilized. For example, quantum cascade lasers (QCL) and interband cascade lasers (ICL) may be utilized at different wavelengths. Additional examples include quinary material (e.g., AlGaInAsSb) that may be used at higher temperatures than a quartemary (e.g., GaInAsSb) type-II structure.

In one implementation, the contact stripes may have a width of from about 1 to about 25 μm, for example, about 25 μm, and may be formed on a pitch of about 100 μm. In one implementation the contacts comprise three layers of metal, including Ti, Pt, and Au, for example at 20 nm, 150 nm and 100 nm thickness, respectively.

Returning to the laser chip 200 of FIG. 2, in either case of optical or electrical pumping, a pumped stripe 203 produces a spatially varying output 207. In an example, a wavelength of the output beam is selectively adjustable to any specific wavelength within a range. This range depends on growth parameters, but may be in the range of, for example, about 3.2 microns to about 3.5 microns. Thus, the photonics source of the embodiments in combination with a sensor may be configured to detect any target gas of that has an absorption falling within this range such as for the C—H stretch region of around 3.3 microns. It is noted, however, that, the embodiments are not so limited any the range can be easily changed to different spectral regions.

Integrated Optic Chip

Figure 3:
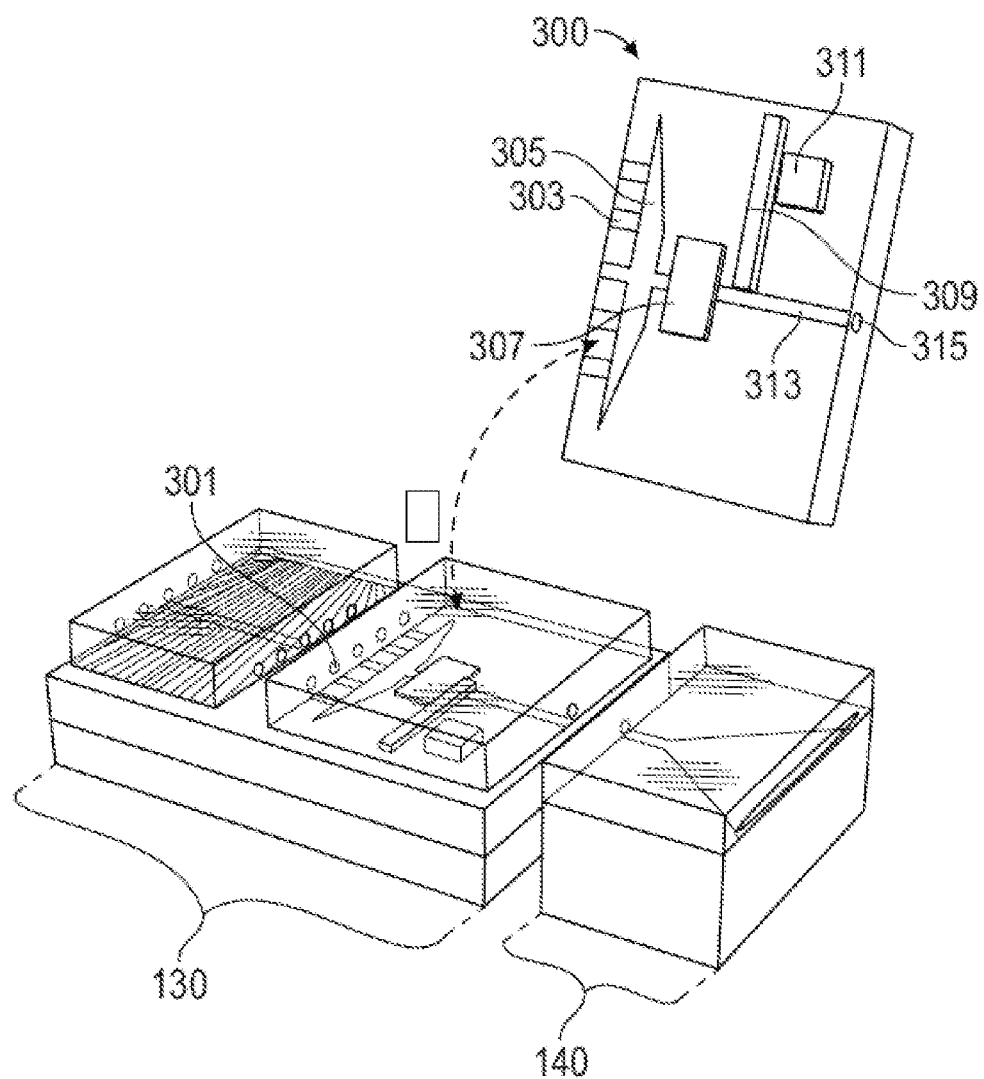
FIG. 3 shows a detailed view of an optics chip component in the integrated system of FIG. 1.

As shown in more detail in FIG. 3, the integrated optic chip 300 may include an array waveguide (AWG) 305, a modulator 307, a gas filled cell 309 and an acoustic wave detector 311. The AWG 305 can accept the spatially varying output 207 of the laser chip 200, for example, at a plurality of waveguides 303 and funnel it into a single waveguide 313. In an example, the AWG 305 can funnel output 207 having a wavelength of up to about 4 microns. In such an example, include a silicon-on-insulator material with silicon as the core of the waveguide and SiO2 as the cladding on either side of the silicon, however other dielectrics may be used. In other examples, the waveguide can funnel output having longer wavelengths, such as wavelengths of greater than about 4 microns. At such longer wavelengths, other materials having a much lower index contrast, such as GaAs and InGaAs, may be used as the cladding layers for the array waveguide 305 so as to provide shallower bends in the waveguides 303.

Once in single waveguide 313, the output is provided to modulator 307 to control the amplitude or intensity of the output, for example, a low noise portion of the spectral output, which may be in the kHz to MHz region. In an example, the modulator 307 may be, for example a Mach-Zehnder modulator. For example, utilizing carrier injection/depletion in silicon as the modulation mechanism allows a higher index change and provides for a device having a decreased size.

A beam splitter can be utilized to divert a sample portion of light exiting the modulator in waveguide 313 through gas filled cell 309 to the acoustic wave detector 311, which may be a surface acoustic wave (SAW) sensor. The gas filled cell may be hermetically sealed and can contain a preselected reference gas, for example, any hydrocarbon gas, such as methane. The reference gas may be maintained at atmospheric pressure within the gas filled cell. As the sample laser output from the modulator is diverted by a beam splitter, it penetrates through the gas filled cell 309 and the gas therein absorbs at least a portion of the sample laser output via, for example, C—H stretch. In an embodiment, the gas in the gas filled cell 309 is at atmospheric pressure.

The acoustic wave detector 311 monitors the absorption in the gas filled chamber. In an example, the acoustic wave detector 311 comprises a transducer that has interdigitated fingers matched to the modulation frequency of light exiting the modulator. In an embodiment, the interdigitated finger device is formed by deposition on a silicon/silicon diode wafer in the silicon based driver electronics of layer 133. Suitable acoustic wave detectors of the embodiments are known in the art. An optional Fabry-Perot resonator can be included to provide wavelength calibration between the absorption lines of the gas filled cell 309.

Power Amplifier

Figure 4:
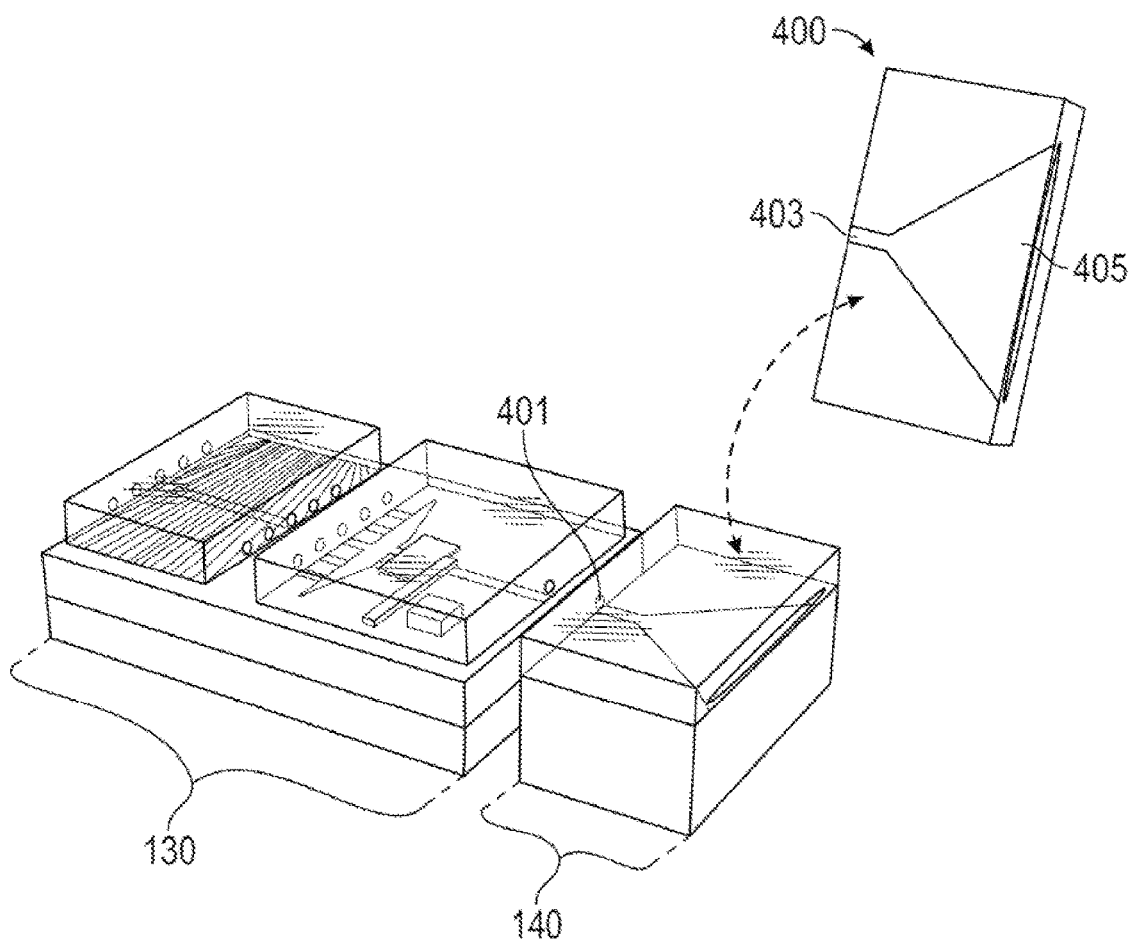
FIG. 4 shows a detailed view of an optional power amplifier component in the integrated system of FIG. 1.

As described above, the integrated photonics system can include an amplifier 400 which is shown in more detail in FIG. 4. The power amplifier 400 may be, for example, a III-V power amplifier. In an embodiment, the power amplifier 400 is disposed on a heat sink 141. The heat sink provides for the dissipation of excess heat resulting from the delivery of power to the chip. In an example, the heat sink can comprise a silicon substrate and may have a thickness of from about 300 microns to about 500 microns in order to conduct the thermal energy away from the amplifier chip.

As shown in more detail in FIG. 4, the power amplifier 400 may also include a varying cross section (fan-shaped portion 405) to provide unidirectional gain while any reflected power from the end facet is directed away from the narrower gain region at the entrance port 403 of the amplifier 400.

It is noted that amplifier 400 may be integrated with silicon based driver electronics of layer 133 along with laser chip 200 and optic chip 300.

Method of Making Electrically Pumped Tunable Laser Chip

As described above, a tunable DFB laser device may comprise the three-layer slab waveguide comprising a substrate 501 (e.g., bottom cladding layer), a core 503 (i.e., an active portion) and a top cladding layer 505 having a DFB chirped grating formed into the top cladding layer. Such a three-layer slab waveguide may be formed according to known methods. The core comprises an active portion of the device and may include at least electrical contacts, such as top and bottom contacts, and a gain medium. Additional layers may be included in the active portion. For example, for interband cascade there are complex layers to align the various band gaps of the materials in those layers. As also described for FIG. 5C, such a tunable DFB laser device may be electrically pumped with the addition of a plurality of separated contact stripes 507 incorporated with the laser device, for example, as top contacts.

Figure 6A:
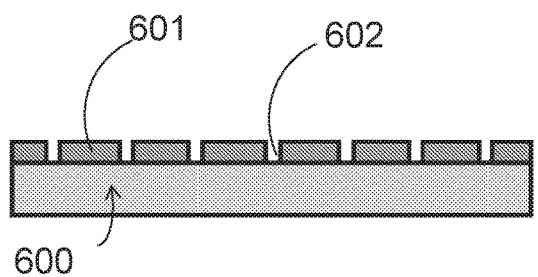
FIGS. 6A-6D show cross section views of a method for fabricating a tunable laser of the embodiments.
Figure 7A:
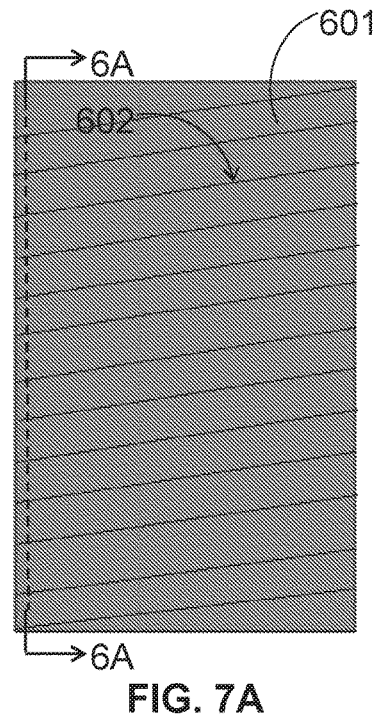
FIGS. 7A-7D show overhead views of a method for fabricating a tunable laser of the embodiments corresponding to the cross sectional views of FIGS. 6A-6D.

Such a three-layer slab waveguide having the DFB chirped grating can be formed by known methods. For example, the chirped grating can be formed by patterning on the top cladding layer using interferometric lithography in photoresist which may then be transferred into the top clad of the slab waveguide using Cl-based ICP etching. The plurality of separated contact stripes can be formed according to a method illustrated in the cross-sectional views of FIGS. 6A-6D, corresponding overhead views in FIGS. 7A-7D, and additional steps illustrated in FIGS. 7E-7F. That is, in a method of forming a tunable laser device, as shown in the cross-sectional view illustrated in FIG. 6A (as viewed according to line 6A-6A in top view FIG. 7A), a laser structure 600 is provided. Laser structure 600 may be similar to that of the three layer waveguide structure of tunable laser 500 in FIG. 5A and may comprise a substrate, an active portion disposed on the substrate, and a chirped distributed feedback (DFB) grating disposed on the active portion as described above.

Figure 6B:
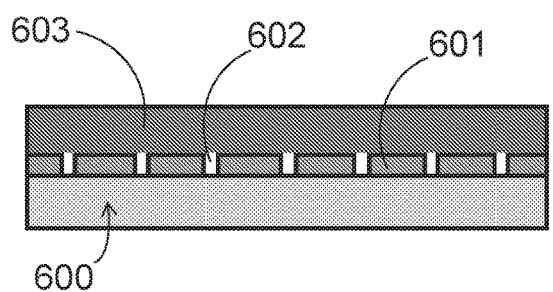
Figure 7B:
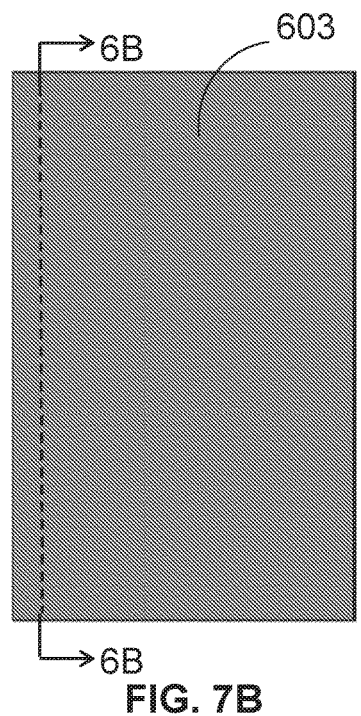

The method continues by forming a contact layer 601 on the laser structure, the contact layer 601 comprising a doped semiconductor medium. In an example, the contact layer can comprise a highly doped semiconductor medium Subsequently, as shown in FIG. 6B (as viewed according to line 6B-6B in top view FIG. 7B), the method continues by patterning current blocking sections (e.g., current confinement grooves 602) into the contact layer 601, for example, by etching through the contact layer to a depth of about 90 nm. In an embodiment, therefore, the contact layer is segmented and the segment portions of which are separated by the current confinement grooves. The current blocking sections formed by current confinement grooves 602 may have widths of from about 1 µm to about 2 µm on 100 µm centers These current confinement grooves 602 may be rotated relative to an edge of the laser device, such as by 6°, to reduce the impact of facet reflections on the device performance as described above.

A higher index blanket layer 603, for example a 100 nm thick Ge layer, may be added above the contact layer. The functionality of blanket layer 603 is to control the mode profile to ensure an appropriate coupling constant for the DFB grating.

A chirped grating 603' is etched into the blanket layer 603 and (as in and/or) the contact layer to form the DFB structure. The grating chirp is adjusted so as to be primarily a transverse chirp (e.g. different periods in the cut 6C as this cut is translated vertically along the top view FIG. 7c. The transverse chirp along the cut 6C-6C is minimized to allow the full width of the laser gain medium to participate in the lasing.

Figure 6C:
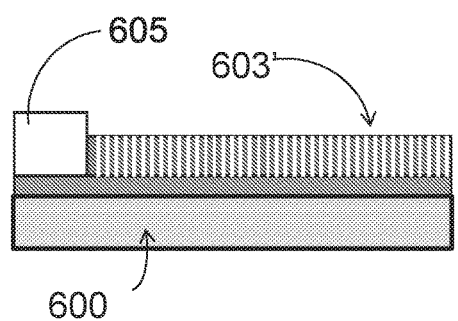
Figure 7C:
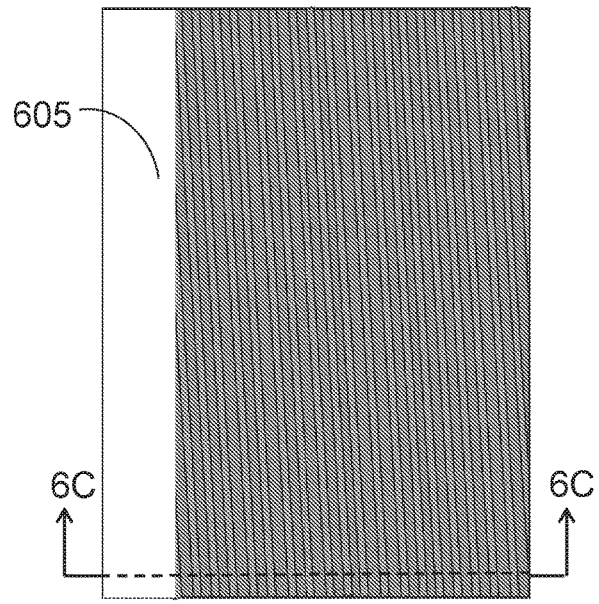
Figure 6D:
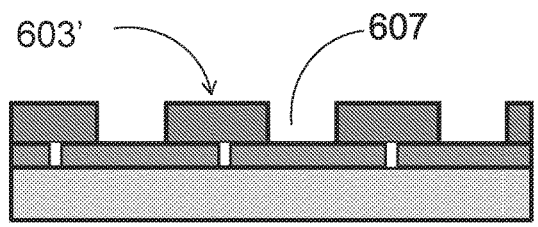

Also, as shown in FIG. 6C (as viewed according to line 6C-6C in FIG. 7C), a portion of the blanket layer, for example, a 500 mm wide strip adjacent the edge of the device is removed to form a contact pad isolation portion on which an insulator layer 605 can be deposited thereon. The contact pad isolation portion can serve to isolate contact pads formed thereon from an underlying semiconductor substrate in order to eliminate gain under the pads. As shown in FIG. 6D (as viewed according to line 6D-6D in FIG. 7D), another etch of the blanket layer is performed, for example, at locations 607, thereby forming localized contact regions where the separated contact stripes will subsequently be formed.

Figure 7D:
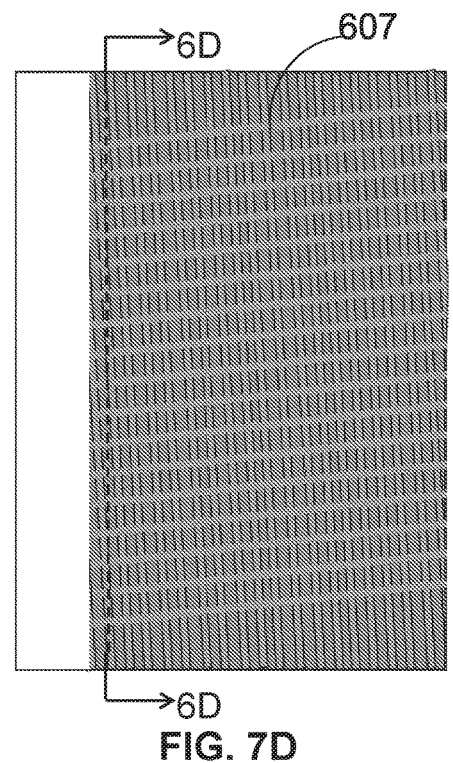
Figure 7E:
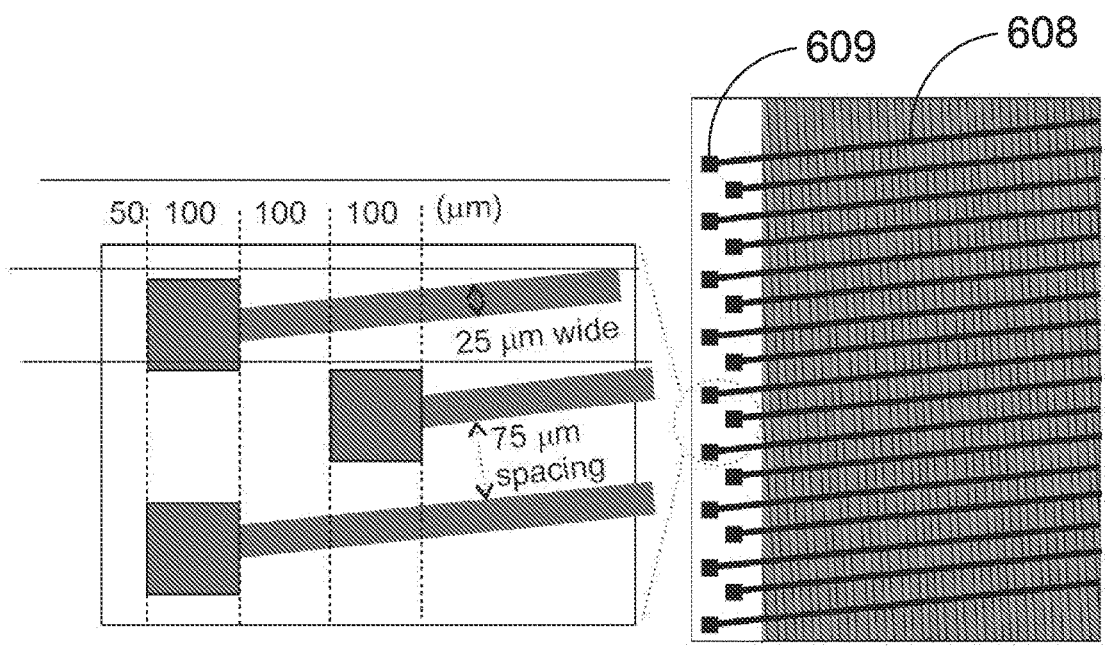
FIGS. 7E-7F show overhead views of additional steps in the method for fabricating a tunable laser of the embodiments followings the steps shown in FIGS. 7A-7D.
Figure 7F:
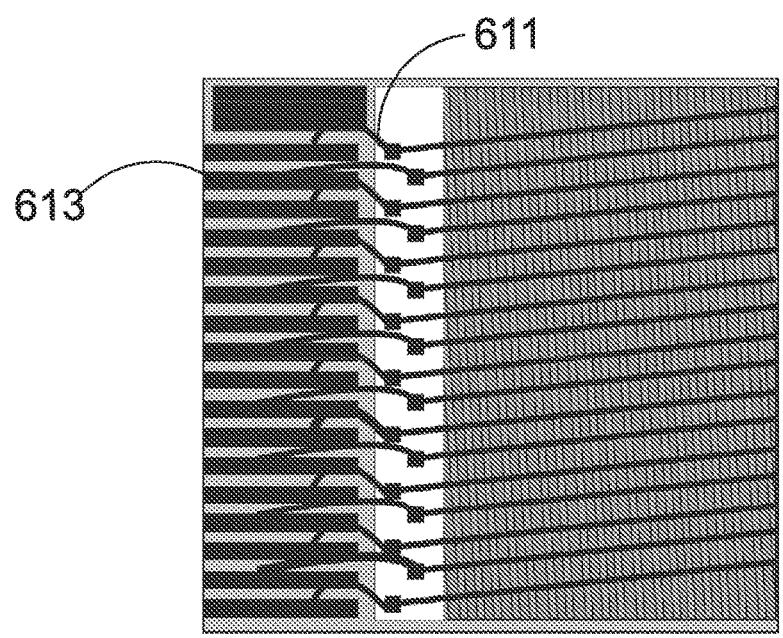

As shown in FIG. 7E, a plurality of separated contact stripes (i.e., contact bars) are then formed in the etched portions formed as described for FIGS. 6D/7D. The separated contact stripes may each have a width of about 25 µm and formed on a 100 µm pitch. The contact stripes may be formed by depositing layers of Ti, Pt, Au, for example at thicknesses of about 20 nm, 150 nm and 100 nm, respectively. As also shown in FIG. 7E, the plurality of contact stripes each terminate at a contact pad 609 The contact pads may have dimensions of about 100×100 µm$^2$ and are formed over the oxide 605. Subsequently, the plurality of separated contact stripes may be electrically connected to a controller (not shown) such that they are individually addressable by the controller as described above for the electronically pumped laser. Accordingly, a backside contact may be formed on the laser device which can be thinned, cleaved and annealed. The backside contact may comprise Cr, Sn, Pt, Au at thicknesses of 30 nm, 40 nm, 150 nm and 100 nm, respectively and the anneal may be performed at 300° C. for about 1 minute in an inert gas environment. The plurality of separated contact stripes 608 may be electrically connected to the controller by wire bonding each pad 609 to a respective one of a backside contact 613 as shown in FIG. 7F. Additionally, the laser device, may be bump bonded to the underlying driver electronics, thereby forming a bump-bonded laser chip which may be a bump-bonded III-V laser chip.

It is noted that the separated contact stripes can be disposed at locations 607 formed by forming localized contact regions. The localized contact regions are formed by etching through the blanket layer to the underlying contact layer, for example, as shown between FIGS. 6D/7D and 7E, and described above. In an alternative embodiment, the separated contact stripes can be disposed over the grating region (e.g., on top of the gratings) with portions of the contacts extending between gratings in the blanket layer and contacting the contact layer. By this alternative embodiment, the step of etching the blanket layers to form localized contact regions at locations 607, as captured in FIGS. 6D/7D, may be eliminated because the separated contact stripes are formed by depositing patterned ones of the separated contact stripes through, for example, a patterned mask.

While the embodiments have been illustrated respect to one or more implementations, alterations and/or modifications can be made to the illustrated examples without departing from the spirit and scope of the appended claims. In addition, while a particular feature of the embodiments may have been disclosed with respect to only one of several implementations, such feature may be combined with one or more other features of the other implementations as may be desired and advantageous for any given or particular function.

Furthermore, to the extent that the terms "including", "includes", "having", "has", "with", or variants thereof are used in either the detailed description and the claims, such terms are intended to be inclusive in a manner similar to the term "comprising." As used herein, the phrase "one or more of", for example, A, B, and C means any of the following: either A, B, or C alone; or combinations of two, such as A and B, B and C, and A and C; or combinations of three A, B and C.

Other embodiments will be apparent to those skilled in the art from consideration of the specification and practice of the descriptions disclosed herein. It is intended that the specification and examples be considered as exemplary only, with a true scope and spirit of the embodiments being indicated by the following claims.

What is claimed is:
1. A tunable laser device, comprising:
a laser structure; and
a plurality of individually addressable, separated contact stripes disposed on the laser structure,
wherein the laser structure comprises:
a substrate, an active portion disposed on the substrate, wherein the active portion comprises at least top and bottom contact layers and a gain medium, and a chirped distributed feedback (DFB) grating comprising a plurality of grating lines and disposed on the active portion, wherein the plurality of separated contact stripes are normal to the plurality of grating lines of the chirped DFB grating.

2. The tunable laser device of claim 1, wherein the plurality of separated contact stripes are disposed on the chirped DFB grating.

3. The tunable laser device of claim 1, wherein the plurality of separated contact stripes are disposed between the chirped DFB grating and the active portion.

4. The tunable laser device of claim 1, further comprising a controller in electrical communication with the plurality of separated contract stripes.

5. The tunable laser device of claim 4, wherein the plurality of separated contact stripes are individually addressable by the controller.

6. The tunable laser device of claim 4, wherein the controller is configured to apply a first current to a first one of the plurality of contact stripes and a second current to a second one of the contact stripes.

7. The tunable laser device of claim 4, wherein the controller is configured to provide a distribution of currents in different ones of the plurality of contact stripes.

8. The tunable laser device of claim 1, wherein the plurality of contact stripes serve as a plurality of pump fingers for electrical pumping of the laser structure.

9. The tunable laser device of claim 1, wherein the chirped DFB grating comprises a grating pitch that varies across the laser structure and is characterized by both longitudinal and transverse chirp parameters.

10. The tunable laser device of claim 1, wherein grating lines of the chirped DFB grating comprises a degree of tilt sufficient to suppress a Fabry-Perot mode.

11. The tunable laser device of claim 1, wherein the DFB grating comprises a degree of tilt sufficient to eliminate facet reflections.

12. The tunable laser device of claim 1, wherein the chirped DFB grating is formed by etching into a material of a clad layer of the laser structure, wherein the material comprises one or more of Ge, GaSb, AlGaSb, AlAsSb, AlGaAsSb, InAlAsSb, GaAlAsSb, AlSb, AlInSb, AlSbAs, or AlGaSbAs.

13. The tunable laser device of claim 1, wherein the laser structure comprises one or more type-II quantum well active regions and is configured to provide optical gain is in the mid-infrared spectral region.

14. A method of operating a tunable laser device, comprising:
electrically pumping a laser structure, the laser structure comprising:
a substrate,
an active portion disposed on the substrate, wherein the active portion comprises at least top and bottom contact layers and a gain medium, and
a chirped distributed feedback (DFB) grating comprising a grating pattern and disposed on the active portion,
wherein the electrically pumping of the laser structure comprises applying a distribution of currents to different ones of a plurality of separated contact stripes disposed on the laser structure and normal to the grating pattern.

15. A method of forming a tunable laser device, comprising:
providing a laser structure comprising:
a substrate,
an active layer disposed on the substrate, and
a chirped distributed feedback (DFB) grating disposed on the active layer;
forming a contact layer on the laser structure, the contact layer comprising a doped gain medium;
forming a blanket layer on the contact layer;
patterning the blanket layer into a grating pattern by etching portions thereof to expose the contact layer; and
forming a plurality of separated contact stripes on the laser structure substantially normal to the grating pattern.

16. The method of claim 15, further comprising:
electrically connecting at least some of the plurality of separated contact stripes to a controller such that they are individually addressable by the controller.

17. The method of claim 16, further comprising removing a portion of the blanket layer to form a contact pad isolation portion.

18. The method of claim 17, further comprising:
depositing an insulator at the contact pad isolation portion, wherein the plurality of separated contact stripes each terminate at respective one of a contact pad formed at the contact pad isolation portion; and
electrically connecting at least some of the plurality of separated contact stripes to a controller such that they are individually addressable by the controller, wherein the electrically connecting comprises wire bonding to a respective one of a backside contact.

19. The method of claim 15, wherein the providing of the laser structure comprises:
forming the active layer on the substrate;
forming a top clad layer on the active layer; and
forming the DFB grating by patterning the top clad layer.

20. An integrated photonics laser source, comprising:
a laser chip that provides a spatially varying electromagnetic output, the laser chip comprising an electronically pumped laser source having a plurality of individually addressable, separated contact stripes formed thereon; and
an integrated optic Si/III-V chip, comprising:
an array waveguide (AWG) that takes the spatially varying output of the laser chip and funnels it into a single waveguide,
a modulator for modulating a frequency of electromagnetic energy from the single waveguide,
a beam splitter that redirects the electromagnetic output from the modulator,
a reference gas disposed in a hermetically sealed gas cell for absorbing at least some of the redirected electromagnetic output, and
an acoustics detector for monitoring absorption of the reference gas; and a power amplifier.

21. The laser source of claim 20, wherein the modulator comprises a Mach-Zehnder modulator.

22. The laser source of claim 20, wherein the reference gas comprises a hydrocarbon gas.

23. The laser source of claim 22, wherein the hydrocarbon gas comprises methane.

24. The laser source of claim 20, wherein the reference gas disposed in the sealed gas cell is maintained at atmospheric pressure.

25. The laser source of claim 20, wherein the acoustics detector comprises an interdigitated finger device matched to the modulation frequency.

26. The laser source of claim 20, further comprising a Fabry-Perot resonator to provide wavelength calibration between absorption lines of the gas cell.

27. The laser source of claim 20, wherein the laser chip comprises a tunable laser.

28. The laser source of claim 27, wherein the tunable laser comprises a chirped grating to provide continuous tuning of a broadband gain medium.

29. The laser source of claim 28, wherein the tunable laser comprises a plurality of pump fingers for electrical pumping.

30. The laser source of claim 20, wherein the laser chip comprises a bump-bonded III-V laser chip.

31. A method for photonically sensing chemicals, comprising:
   providing an integrated photonics chemical source, the source comprising:
      a laser chip that provides a spatially varying electromagnetic output,
      an integrated optic Si/III-V chip, and
      a power amplifier,
      wherein the laser chip comprises a chirped grating to provide continuous tuning of a broadband gain medium, a plurality of separated contact stripes, and a plurality of pump fingers for electrical pumping, and
      wherein the integrated optic Si/III-V chip comprises:
         a modulator for modulating a frequency of electromagnetic energy from the laser chip,
         a beam splitter that redirects the electromagnetic output from the modulator,
         a reference gas disposed in a hermetically sealed gas cell for absorbing at least some of the redirected electromagnetic output, and
         an acoustics detector for monitoring absorption of the reference gas; and
   pumping two or more separated groups of stripes at the same time.

32. The method of claim 31, wherein the integrated optic Si/III-V chip further comprises an array waveguide (AWG) that takes the spatially varying output of the laser chip and funnels it into a single waveguide.

33. The method of claim 31, wherein the modulator comprises a Mach-Zehnder modulator.

34. The method of claim 31, wherein the reference gas comprises a hydrocarbon gas.

35. The method of claim 34, wherein the hydrocarbon gas comprises methane.

36. The method of claim 31, wherein the reference gas disposed in the sealed gas cell is maintained at atmospheric pressure.

37. The method of claim 31, further comprising electrically connecting at least some of the plurality of separated contact stripes to a controller such that they are individually addressable by the controller, wherein the acoustics detector comprises an interdigitated finger device matched to a modulation frequency.

38. The method of claim 31, further comprising a Fabry-Perot resonator to provide wavelength calibration between absorption lines of the gas cell.

39. The method of claim 31, further comprising a power amplifier.

* * * * *